United States Patent [19]  [11] Patent Number: 4,960,789
Wollweber et al.  [45] Date of Patent: Oct. 2, 1990

[54] 3-CYANO-4-PHENYL-PYRROLES

[75] Inventors: Detlef Wollweber, Wuppertal; Wilhelm Brandes, Leichlingen, both of Fed. Rep. of Germany

[73] Assignee: Bayer Aktiengesellschaft, Leverkusen, Fed. Rep. of Germany

[21] Appl. No.: 266,966

[22] Filed: Nov. 3, 1988

[30] Foreign Application Priority Data

Nov. 9, 1987 [DE] Fed. Rep. of Germany .... 3737984.4

[51] Int. Cl.$^5$ ................... A01N 47/40; C07D 207/34; C07B 37/10; C07C 121/70
[52] U.S. Cl. ..................................... 514/427; 548/561; 558/401
[58] Field of Search ........................ 548/561; 514/427

[56] References Cited

U.S. PATENT DOCUMENTS 3,590,051  6/1971  Gorman et al. ................... 260/326.9
4,705,801 11/1987  Martin II ............................ 548/561
4,709,053 11/1987  Martin I .............................. 548/561

FOREIGN PATENT DOCUMENTS 0236272  9/1987  European Pat. Off. .
2927480  1/1980  Fed. Rep. of Germany .
61-30571  2/1986  Japan ................................... 548/561

Primary Examiner—Mark L. Berch
Attorney, Agent, or Firm—Sprung, Horn Kramer & Woods

[57] ABSTRACT 3-cyano-4-phenyl-pyrroles of the formula

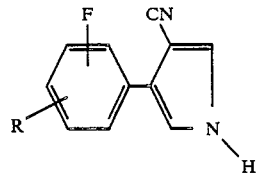

in which
R stands for halogen, alkyl, alkoxy, alkylthio, halogenoalkyl, halogenoalkoxy or halogenoalkylthio, have been found. These compounds are useful as fungicides.

6 Claims, No Drawings

3-CYANO-4-PHENYL-PYRROLES AS FUNGICIDES

The invention relates to new 3-cyano-4-phenylpyrroles, to a process for their preparation, to their use as pesticides, and to new intermediates.

It has been disclosed that certain 3-cyano-4-phenyl-pyrroles, such as, for example, the compound 3-cyano-4-(2,3-dichlorophenyl)-pyrrole, possess fungicidal activity (cf., for example, EP 236,272).

However, the activity of these previously known compounds is not completely satisfactory in all fields of application, in particular at low application rates and concentrations.

New 3-cyano-4-phenyl-pyrroles of the general formula (I)

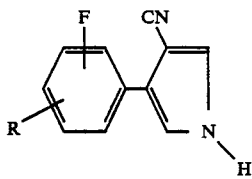

in which
  R stands for halogen, alkyl, alkoxy, alkylthio, halogenoalkyl, halogenoalkoxy or halogenoalkylthio,
have been found.

Furthermore, it has been found that the new 3-cyano-4-phenyl-pyrroles of the general formula (I)

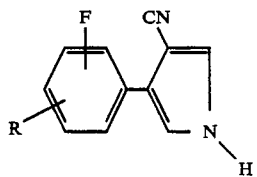

in which
  R stands for halogen, alkyl, alkoxy, alkylthio, halogenoalkyl, halogenoalkoxy or halogenoalkylthio,
are obtained when substituted fluorocinnamonitriles of the formula (II)

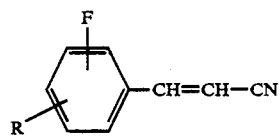

in which
  R has the abovementioned meaning,
are reacted with sulphonylmethyl isocyanides of the formula (III)

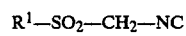

$$R^1-SO_2-CH_2-NC \qquad (III)$$

in which
  $R^1$ stands for alkyl or for optionally substituted aryl,
in the presence of a base and if appropriate in the presence of a diluent.

Finally, it has been found that the new 3-cyano-4-phenyl-pyrroles of the general formula (I) possess good action against pests.

Surprisingly, the 3-cyano-4-phenyl-pyrroles of the general formula (I) according to the invention show a considerably better fungicidal activity than, for example, the 3-cyano-4-phenyl-pyrroles known from the prior art which are chemically similar compounds of a similar type of action, such as 3-cyano-4-(2,3-dichlorophenyl)-pyrrole.

Formula (I) provides a general definition of the 3-cyano-4-phenyl-pyrroles according to the invention. Preferred compounds of the formula (I) are those in which
  R stands for fluorine, chlorine, bromine, iodine, for in each case straight-chain or branched alkyl, alkoxy or alkylthio, each having 1 to 4 carbon atoms, or stands for in each case straight-chain or branched halogenoalkyl, halogenoalkoxy or halogenoalkylthio, each having 1 to 4 carbon atoms and 1 to 9 identical or different halogen atoms.

Particularly preferred compounds of the formula (I) are those in which
  R stands for fluorine, chlorine, bromine, methyl, ethyl, methoxy, ethoxy, methylthio, trifluoromethyl, trifluoromethoxy or trifluoromethylthio.

Very particularly preferred compounds of the formula (I) are those in which
  R stands for fluorine, chlorine, methyl, trifluoromethyl or trifluoromethoxy.

In addition to the compounds mentioned in the preparation examples, the following 3-cyano-4-phenylpyrroles of the general formula (I) may be mentioned individually:

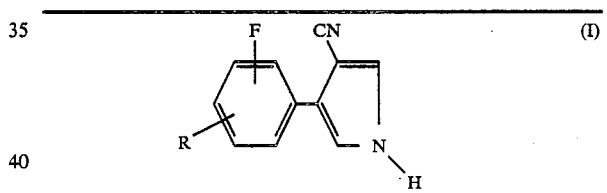

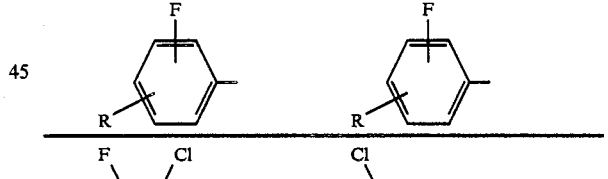

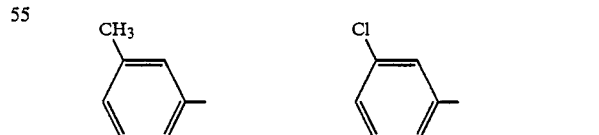

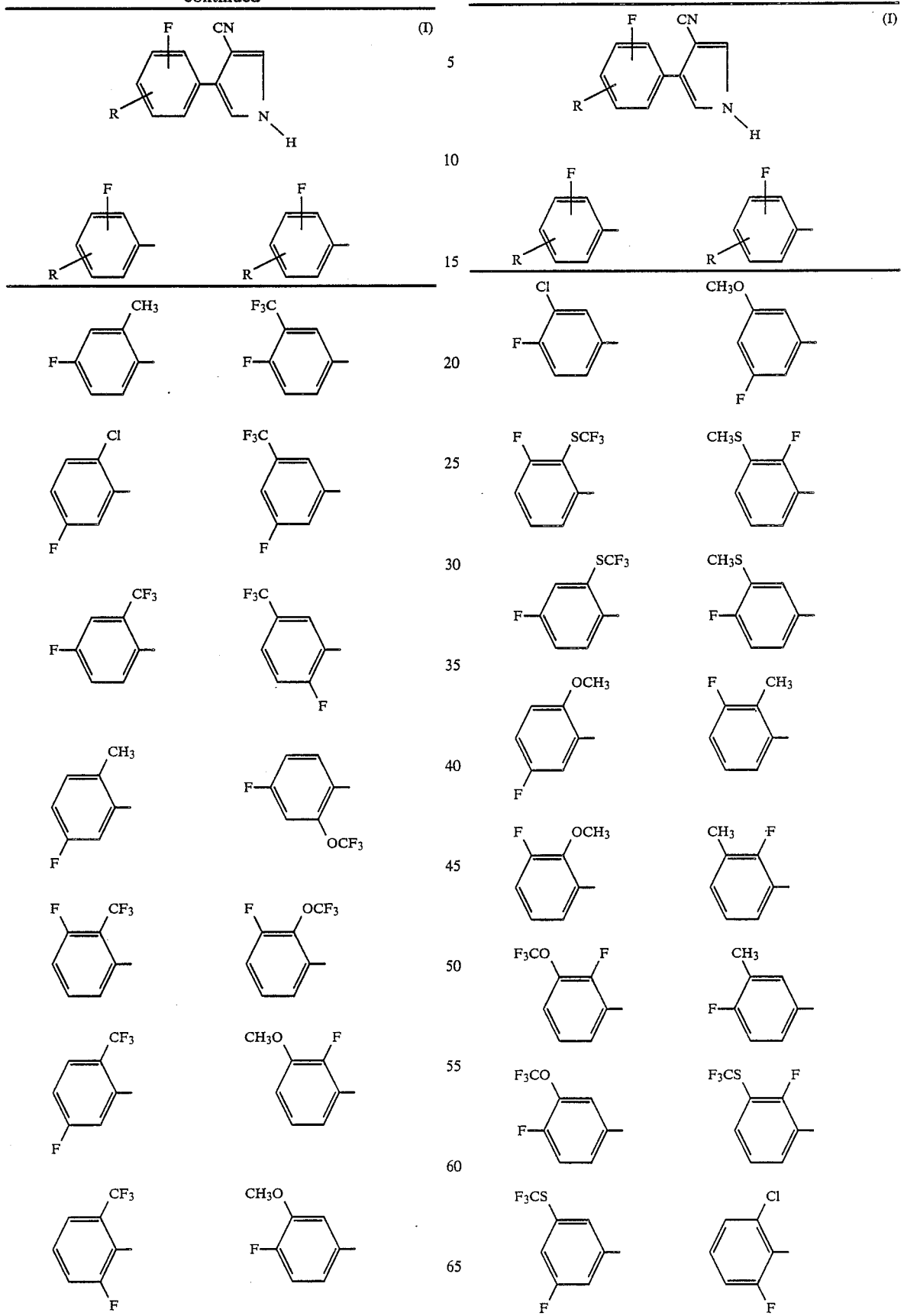

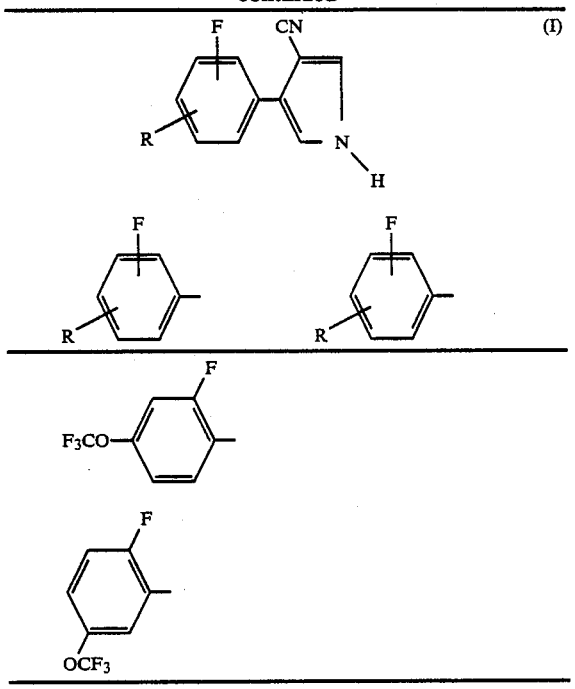

If, for example, 3-chloro-2-fluorocinnamonitrile and p-toluenesulphonylmethyl isocyanide are used as the starting substances and sodium hydride is used as the base, the course of reaction of the process according to the invention can be represented by the following equation:

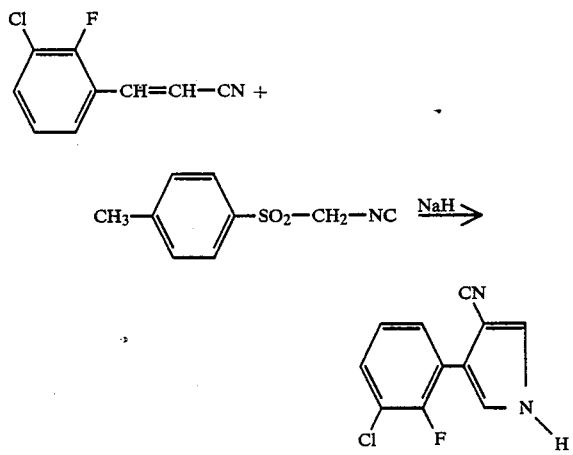

Formula (II) provides a general definition for the substituted fluorocinnamonitriles required as starting substances for carrying out the process according to the invention. In this formula (II), R preferably stands for those radicals which have already been mentioned in connection with the description of the substances of the formula (I) according to the invention as being preferred for this substituent.

The substituted fluorocinnamonitriles of the formula (II) are new. However, they are obtained in analogy with known processes (cf., for example, DE-OS (German Published Specification) 2,927,480), for example when a) fluoroanilines of the formula (IV)

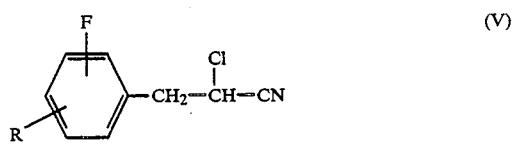

in which

R has the abovementioned meaning, are, initially in a first step, reacted with acrylonitrile under the customary conditions for diazotization, for example in the presence of sodium nitrite and hydrochloric acid, and in the presence of a suitable metal salt catalyst, such as, for example, copper(II) chloride or copper(II) oxide, and if appropriate in the presence of a suitable diluent, such as, for example, acetone or water, at temperatures between −20° C. and 50° C. ("Meerwein arylation"; cf., in this context, also Organic Reactions 11, 189 [1960]; Organic Reactions 24, 225 [1976]or C. Ferri "Reaktionen der organischen Synthese" [Reactions of Organic Synthesis]p. 319, Thieme Verlag Stuttgart 1978), and then, in a 2nd step, the substituted α-chloro-β-phenylpropionitriles of the formula (V) thus obtainable

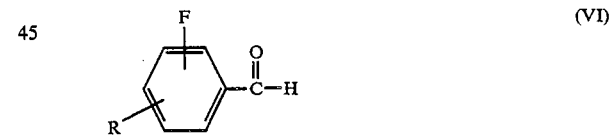

in which

R has the abovementioned meaning, are dehydrohalogenated (cf. also the preparation examples) with bases, such as, for example, triethylamine or diazabicycloundecene, in a customary manner at temperatures between 0° C. and 50° C., if appropriate in the presence of a diluent, such as, for example, tetrahydrofuran, or, alternatively, when b) fluorobenzaldehydes of the formula (VI)

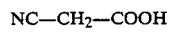

in which

R has the abovementioned meaning, and cyanoacetic acid of the formula (VII)

NC—CH₂—COOH          (VII)

are, in a customary manner, subjected to a condensation reaction at temperatures between 50° C. and 120° C., in the presence of a base, such as, for example, piperidine or pyridine, and if appropriate in the presence of a suitable diluent, such as, for example, pyridine, with simultaneous decarboxylation (cf., for example, "Organikum", p. 571/572; 15th edition; VEB Deutscher Verlag der Wissenschaften Berlin 1981, and the preparation examples).

Some of the fluoroanilines of the formula (IV) are known (cf., for example, J. org. Chem. 39, 1758-1761 [1974]; J. med. Chem. 12, 195-196 [1969]or US-PS (U.S.

Patent Specification No.) 3,900,519) or can be obtained in analogy with known processes.

New compounds of the formula (IVa)

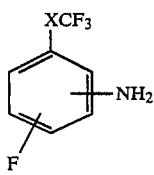

are, for example, those in which

X stands for oxygen or sulphur.

They are the subject-matter of a separate patent application of the applicant, not belonging to the prior art (cf. German Patent Application No. P 37 37 985 dated Nov. 9, 1987 which corresponds to U.S. Patent application Ser. No. 264,462, filed on Oct. 28, 1988, now pending.

Compounds of the formula (IVa) which are preferred are 2-fluoro-5-amino-fluoromethylthio-benzene, 2-fluoro-4-amino-fluoromethoxy-benzene, 3-amino-4-fluorotrifluoromethoxy-benzene, 2-amino-4-fluoro-trifluoromethoxy-benzene and 2-amino-5-fluoro-trifluoromethoxybenzene.

A generally applicable process for the preparation of compounds of the formula (IVa)

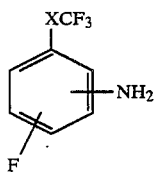

in which

X stands for oxygen or sulphur, is characterized in that compounds of the formula (VIII)

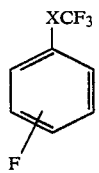

in which

X has the meaning given for formula (IVa), are nitrated and the nitro compounds thus obtained are reduced.

The fluorine-containing trifluoromethoxy- and trifluoromethylthiobenzenes to be employed in this process are known (J. Org. Chem. 29, 1, 1964).

Nitration can be carried out using customary nitrating agents, for example mixture$ of nitric acid and sulphuric acid. In this process, the temperature can be in the range of 0°to 80° C., preferably, it is 20° to 50° C. The nitrating agent can be employed in amounts such that, for example, 0.8 to 1.5 moles of nitrating agent are formed in the reaction mixture per mole of starting compound. Preferably, the amounts are chosen such that 1 to 1.1 moles of nitrating agent are formed per mole of starting compound. If appropriate, nitration is carried out in the presence of an inert organic solvent. A suitable solvent is, for example, dichloromethane.

The subsequent reduction can be carried out chemically, i.e., for example using metals or metal salts having a reducing action. Suitable metals and metal salts are, for example, iron, zinc, tin, tin(II) chloride and titanium(III) chloride. Such reducing agents are preferably employed in the stoichiometrically required amount. In such a reduction, the nitro compounds can, for example, be employed in the state in which they are obtained in the nitrating process, or in which they are isolated afterwards. Alternatively, the reduction can be carried out catalytically using hydrogen, it being possible, for example, to employ catalysts which contain, or consist of, metals. Suitable metals are, for example, the metals of sub-group VIII of the Periodic Table of the Elements, in particular palladium, platinum and nickel. The metals can be present in the elementary form or in the form of compounds, and also in particularly activated forms, for example, in the form of Raney metals, or applied as metals or metal compound on support materials. Raney nickel, palladium-on-charcoal and aluminum oxide are preferred.

The catalytic reduction is preferably carried out in the presence of a solvent. Suitable solvents are, for example, alcohols and ethers, such as methanol, ethanol and tetrahydrofuran. The catalytic reduction can be carried out, for example, at temperatures as indicated in the preparative example and, for example, at hydrogen pressures in the range of 1 to 100 bar. Excess hydrogen is generally not critical.

Preferably, acid-free nitro compounds are employed in the catalytic reduction. If necessary, the latter may, therefore, have to be freed from acids, for example by washing with water or neutralization with a base.

For example, working up of the reaction mixture after the chemical reduction or the catalytic hydrogenation can be carried out such that any solid components are initially filtered off and the filtrate is distilled, if appropriate after washing with water. If an isomer mixture is obtained as the reaction product, the former can be separated by precision distillation.

Compounds of the formula (IVa) having fluorine in the o- or p-position relative to the amino group can also be prepared by reacting compounds of the formula (IX)

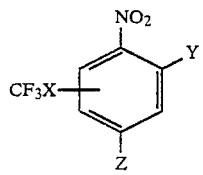

in which

X stands for oxygen or sulphur and at least one of the symbols Y and Z stands for chlorine and the other stands for hydrogen, with fluorination agents, such as potassium fluoride, in the presence of polar aprotic solvents, such as tetramethylene sulphone, in which reaction any chlorine which is present is replaced by fluorine, and by subsequently carrying out a reduction in which the nitro group is converted to an amino group.

Compounds of the formula (IX) are known (cf. Houben Weyl, Methoden der organischen Chemie [Methods of Organic Chemistry]E4, page 633 et seq.)

Tetramethylene sulphone acts as a solvent and is preferably employed in at least an amount such that a reaction mixture is present which can be readily stirred. The reaction is not disturbed by higher amounts of tetramethylene sulphone.

Temperatures suitable for the reaction with potassium fluoride in tetramethylene sulphone are, for example, those in the range of 160° to 230° C. Temperatures of 180° to 210° C. are preferred. The reaction is preferably carried out in an environment which is as far as possible free from water. This can be achieved, for example, by employing the compound of the formula (IX) in carefully dried form as the last component and by removing by distillation, from the other components previously added, a small amount of tetramethylene sulphone together with any water present.

When the reaction is complete, the solids present in the reaction mixture can be removed, and, if appropriate, all, or part of the tetramethylene sulphone.

Subsequent reduction of the nitro group to give the amino group, and working up of the reaction mixture which is then present can be carried out as described above in the generally applicable process for the preparation of these compounds.

Alternatively, compounds of the formula (IVa) in which X=oxygen can be prepared by reacting compounds of the formula (X)

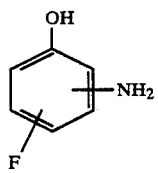

(X)

with carbon tetrachloride in the presence of hydrogen fluoride, in which reaction the OH group is converted to a CF$_3$O group.

Compounds of the formula (X) are known (cf. FR 2,446,805).

For example, it is possible to employ 1 to 10 moles of carbon tetrachloride and 5 to 30 moles of hydrogen fluoride per mole of the respective compound of the formula (X). Likewise, relatively large amounts of excess carbon tetrachloride and hydrogen fluoride do not generally disturb the process. Suitable reaction temperatures are, for example, those in the range of 100 to 150° C. This process is preferably carried out under pressure, for example by releasing the resultant hydrogen chloride gas only above a certain pressure. For example, this can be a pressure of 18 to 60 bar. If appropriate, the pressure can be increased by additionally using an inert gas, for example 1 to 20 bar nitrogen. It is advantageous to stir well during the reaction.

Working up of the reaction mixture can be carried out, for example, by cooling the reaction mixture to room temperature, releasing the pressure, distilling off excess hydrogen fluoride and excess carbon tetrachloride, for example at temperatures up to 80° C., pouring the residue into ice water, rendering the mixture alkaline with sodium hydroxide solution, extracting the organic phase with dichloromethane, and subjecting it, after drying, to precision distillation.

Further new compounds of the formula (IVb)

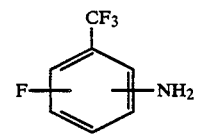

(IVb)

are those in which the trifluoromethyl group is in the 1-position, and the amino group
   a) is in the 2-position and a fluorine atom is in the 6-position, or
   b) is in the 3-position and a fluorine atom is in the 2-position.

They are the subject-matter of an application by the applicant which is not part of the prior art (cf. German Patent Application No. P 37 37 986 dated Nov. 9, 1987which corresponds to U.S. patent application Ser. No. 261,795, filed on Oct. 24, 1988, now pending—.).

A preferred process for the preparation of fluorine-containing trifluoromethylaminobenzenes in which the trifluoromethyl group is in the 1-position, and the amino group
   a) is in the 2-position and a fluorine atom is in the 6-position, or
   b) is in the 3-position and a fluorine atom is in the 2-position is characterized in that corresponding fluorinecontaining trifluoromethylbenzenes are subjected to a nitrating reaction, and the resultant fluorine-containing trifluoromethylnitrobenzenes are reduced.

The trifluoromethylbenzenes to be employed in this process according to the invention, which contain fluorine but are free from amino groups, are known. Nitration, subsequent reduction and working up is carried out under the conditions given in the preparation of compounds of the formula (IVa).

A further process specifically for the preparation of fluorine-containing trifluoromethylaminobenzenes, in which the trifluoromethyl group is in the 1-position, and the amino group
   a') is in the 2-position and a fluorine atom is in the 6-position or
   b') is in the 4-position and a fluorine atom is in the 2-position
is characterized in that corresponding fluorine-containing 2- and/or 4-halogenotrifluoromethylbenzenes are reacted with ammonia under increased pressure and in the presence of an organic solvent.

The 2- and/or 4-halogenotrifluoromethylbenzenes to be employed in this process are known.

It is possible for the ammonia to be added in the liquid or the gaseous form, for example as a substance (gaseous or liquid) or as an aqueous solution. It is, for example, possible to employ 1 to 10 moles of ammonia per mole of halogen atoms in the 2- and/or 4-position to be replaced by NH$_2$ groups. This amount is preferably 3 to 8 moles. Suitable temperatures for this reaction are, for example, those in the range of 80° to 160° C., preferably those in the range of 100° to 130° C. It is possible for the reaction to be carried out under the inherent pressure of the ammonia, appearing at the reaction temperature in the sealed vessel, which pressure can be, for example, in the range of 10 to 20 bar. It is also possible to employ higher pressures, for example pressures up to 100 bar.

Solvents which may be employed for this reaction are inert or substantially inert organic solvents of a wide range of types. Suitable solvents are, for example, alcohols, ethers, sulphones and aromatic hydrocarbons.

The desired reaction product(s) can be obtained, for example, from the reaction mixture present after the reaction by initially cooling and releasing the pressure, then removing the solvent and subsequently carrying out a distillation, preferably under reduced pressure.

Most of the fluorobenzaldehydes of the formula (VI) furthermore required as precursors for the preparation of the new starting products of the formula (II), variant b) are known (cf., for example, Chem. Abstr. 100; 209 388k=Jap. Pat. 58/222 045), thus, 5-fluoro-2-trifluoromethylbenzaldehyde having the Registration No. 90 381-08-1 in Chem. Abstr., 3-chloro-5-fluorobenzaldehyde having the number 90 390-49-1, and 3-chloro-6-fluorobenzaldehyde having the number 96 515-79-6, etc., are mentioned. The cyanoacetic acid of the formula (VII) is likewise a generally known compound of organic chemistry.

Formula (III) provides a general definition for the sulphonylmethyl isocyanides furthermore required as starting substances for carrying out the process according to the invention. In this formula (III), R1 preferably stands for methyl or for optionally monosubstituted phenyl, such as, for example, 4-methylphenyl, 4-chlorophenyl or phenyl.

The sulphonylmethyl isocyanides of the formula (III) are known (cf., for example, Synthesis 1985, 400–402; Org. Syntheses 57, 102–106 [1977]; J. org. Chem. 42, 1153–1159 [1977]; Tetrahedron Lett. 1972, 2367–2368).

Suitable diluents for carrying out the process according to the invention are inert organic solvents. These include in particular aliphatic, alicyclic or aromatic, optionally halogenated, hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran or ethylene glycol dimethyl or diethyl ether, amides, such as dimethylformamide, dimethylacetamide, N-methylformanilide, N-methylpyrrolidone or hexamethylphosphoric triamide, or sulphoxides, such as dimethyl sulphoxide.

If appropriate, the process according to the invention can also be carried out in a two-phase system, such as, for example, water/toluene or water/dichloromethane, if appropriate in the presence of a phase-transfer catalyst. Examples of such catalysts which may be mentioned are: tetrabutylammonium iodide, tetrabutylammonium bromide, tributyl-methylphosphonium bromide, trimethyl-$C_{13}$/$C_{15}$-alkylammonium chloride, dibenzyldimethylammonium methyl sulphate, dimethyl-$C_{12}$/$C_{14}$alkyl-benzylammonium chloride, tetrabutylammonium hydroxide, 15-crown-5, 18-crown-6, triethylbenzylammonium chloride and trimethylbenzylammonium chloride.

The process according to the invention is preferably carried out in the presence of a suitable base. Suitable as such are all inorganic and organic bases which may customarily be used. Preferably, the hydrides, hydroxides, amides, alcoholates, carbonates or hydrogen carbonates of alkali metals are used, such as, for example, sodium hydride, sodium amide, sodium hydroxide, sodium methoxide, sodium ethoxide, potassium t-butoxide, sodium carbonate or sodium hydrogen carbonate, and also tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU).

When carrying out the process according to the invention, the reaction temperatures may be varied within a relatively wide range. In general, the process is carried out at temperatures between $-30°$ C. and $+120°$ C., preferably at temperatures between $-20°$ C. and $+50°$ C.

In carrying out the process according to the invention, 1.0 to 2.0 moles, preferably 1.0 to 1.5 moles, of sulphonylmethyl isocyanide of the formula (III) and 1.0 to 2.0 moles, preferably 1.0 to 1.5 moles, of base are generally employed per mole of substituted fluorocinnamonitrile of the formula (II). In this process, it can be advantageous to carry out the reaction in the presence of a protective gas atmosphere, such as, for example, argon. The reaction is carried out, and the reaction products are worked up and isolated by generally customary methods.

As an alternative to the preparation of the active substances according to the invention with the aid of the preparation process according to the invention, various further preparation processes for the preparation of the active substances according to the invention may be considered.

Thus, for example, active substances of the formula (I) according to the invention are also obtained when α-cyanocinnamic acid esters are reacted with p-toluenesulphonylmethyl isocyanide in the presence of bases and in the presence of copper(II) salts (cf. J6-1030-571 or J6-1200-984), or when α-substituted cinnamonitriles are subjected to a cyclization reaction with isocyanoacetic acid esters in the presence of sodium hydride, the resultant pyrrole-2-carboxylic acid esters are hydrolyzed with bases, and the reaction product is then thermally decarboxylated (cf. JP 59/212 468), or when phenacylamine derivatives are reacted with suitably substituted acrylonitrile derivatives (cf. EP 174,910), or when 3-trifluoromethyl-4-phenyl-pyrroles are reacted with ammonia at an increased temperature and under increased pressure (cf. EP 182,738), or when 3-cyano-4-phenyl-Δ2-pyrrolines are oxidized in the presence of copper(II) salts or iron(III) salts (cf. EP 183,217), or when α-cyanoacrylic acid derivatives are reacted with isocyanoacetic acid esters in the presence of a base, and, in a 2nd step, the resultant Δ2-pyrroline-2-carboxylic acid derivatives are oxidatively decarboxylated in the presence of a base and in the presence of a metal salt catalyst (cf. German Patent Application No. P 3,718,375, dated 02.06.1987).

The active compounds according to the invention show a strong action against pests and can be used in practice for combating undesired harmful organisms. The active compounds are suitable for use as plant protective agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or Ustilago avenae; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention can be used with particularly good success for combating diseases in fruit and vegetable growing, such as, for example, against the causative organism of grey mold of beans (*Botrytis cinerea*) or for combating rice diseases, such as, for example, against the causative organism of blast disease in rice (*Pyricularia oryzae*).

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl sulphonates as well as albumin hydrolyzation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

Preparation Examples

EXAMPLE 1

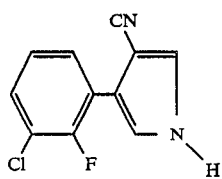

A solution of 6.0 g (0.0331 mole) of 3-(2-fluoro3-chlorophenyl)-acrylonitrile and 7.8 g (0.0431 mole) of p-toluenesulphonylmethyl isocyanide in 20 ml of a mixture consisting of tetrahydrofuran/dimethyl sulphoxide (5:1) are added dropwise and with stirring to 1.4 g (0.0464 mole) of sodium hydride (80% in mineral oil) in 17.5 ml of tetrahydrofuran, at a temperature of −10° C. to −20° C. and under an argon protective gas atmosphere. When the addition is complete, the reaction mixture is allowed to warm to room temperature, water is added, the mixture is extracted several times with ethyl acetate, and the combined ethyl acetate phases are washed with water, dried over sodium sulphate and concentrated in vacuo. The residue is purified by chromatography on silica gel (mobile phase: cyclohexane/ethyl acetate 5:1).

3.3 g (45% of theory) of 3-cyano-4-(2-fluoro-3-chlorophenyl)-pyrrole of melting point 180° C. -181° C. are obtained.

In a corresponding manner and in accordance with the general instructions for the preparation, the following 3-cyano-4-phenyl-pyrroles of the general formula (I) are obtained:

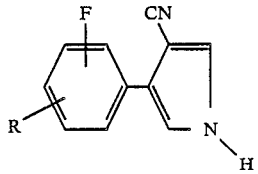

| Example No. | R ![phenyl] | Melting Point [°C.] |
|---|---|---|
| 2 | Cl, F (2-Cl, 4-F phenyl) | 126–128 |
| 3 | F, CH₃ | 133–134 |
| 4 | CH₃, F | 130–131 |
| 5 | F, F | 176–177 |
| 6 | F, F₃CS | 160–161 |

Preparation of the starting compounds

EXAMPLE II-1

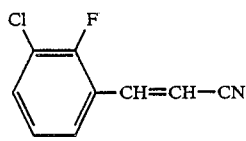

2.5 ml of piperidine and 22.9 g (0.27 mole) of cyanoacetic acid are added to a solution of 40.1 g (0.25 mole) of 2-fluoro-3-chlorobenzaldehyde in 170 ml of pyridine, and the mixture is heated to reflux for 14 hours. For working up, the mixture is concentrated in vacuo, the residue is taken up in ethyl acetate, washed consecutively with 1-normal hydrochloric acid, with aqueous sodium hydrogen sulphite solution as well as with water, dried over sodium sulphate and concentrated in vacuo. The oil remaining can be purified by chromatography on silica gel (mobile phase: cyclohexane/ethyl acetate 5:1).

16.9 g (37% of theory) of 3-(2-fluoro-3-chlorophenyl)-acrylonitrile of melting point 90° C. -92° C. are obtained.

EXAMPLE II-2

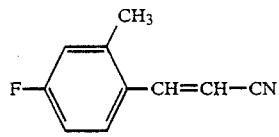

18.2 g (0.12 mole) of diazabicycloundecene in 150 ml of tetrahydrofuran are added dropwise, with stirring at room temperature, to 21.7 g (0.11 mole) of 2-chloro-3-(4-fluoro-2-methylphenyl)-propionitrile in 100 ml of tetrahydrofuran, and when the addition is complete, the mixture is stirred at room temperature for 15 hours and filtered, the filtrate is evaporated in vacuo, the residue is taken up in ethyl acetate, washed consecutively with 1-normal hydrochloric acid and water and dried over sodium sulphate, and the solvent is removed in vacuo. 34.6 g (96% of theory) of 3-(4-fluoro-2-methylphenyl)-acrylonitrile of melting point 86° C.–87° C. are obtained.

In a corresponding manner and in accordance with the general instructions for the preparation, the following fluorocinnamonitriles of the general formula (II) are obtained:

| Example No. | R | physical properties |
|---|---|---|
| II-3 | 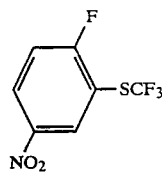 | m.p. 59–60° C. |
| II-4 | 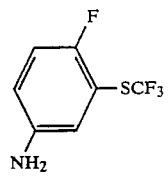 | m.p. 76–77° C. |

EXAMPLE (IV-1)

(a)

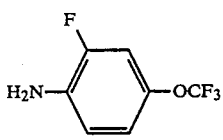

20 g of potassium fluoride are suspended in 100 ml of tetramethylene sulphone, and approximately 20 ml of solvent are distilled off at 15 mbar. 30 g of 3-trifluoromethylmercapto-4-chloro-nitrobenzene are then added, and the mixture is stirred at 190° C. for 6 hours with the exclusion of humidity. When the mixture has cooled to 25° C., it is poured into 300 ml of water and extracted several times with toluene. The toluene phase is washed with water twice, then dried and distilled. At a boiling point of 115° to 120° C. at 18 mbar, 20 g of 2-fluoro-5-nitro-trifluoromethylthiobenzene distil over.

(b)

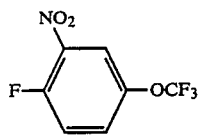

20 g of the nitro compound prepared in a) are introduced into a stirring apparatus together with 10 ml of dioxane, 150 ml of water, 17 g of iron powder and 2 g of ammonium chloride, and the mixture is then refluxed for 5 hours. The solution is cooled and filtered, and the filter residue is washed several times with dichloromethane. The product is extracted from the aqueous phase using dichloromethane, and the combined organic phases are dried and freed from the solvent. Precision distillation of the product yields 14 g of 2-fluoro-5-aminotrifluoromethylthio-benzene of boiling point 112 to 114° C. at 16 mbar.

EXAMPLE IV-2

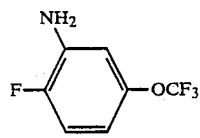

100 g of 2-fluoro-4-hydroxy-aniline, 500 ml of anhydrous hydrogen fluoride and 500 ml of tetrachloromethane are introduced into a fluorination apparatus, and 3 bar of nitrogen are forced in. The mixture is then heated at 120° C. for 7 hours with stirring at 400 rpm, and the resultant hydrogen chloride is continuously released at 38 bar. When the reaction is complete, the mixture is cooled to 20° C., the pressure is released, and excess hydrogen fluoride is distilled off together with carbon tetrachloride up to 80° C. After cooling, the residue is poured into 500 ml of ice water and rendered alkaline with sodium hydroxide solution, with cooling. The organic phase is then extracted with dichloromethane, dried, and subjected to precision distillation in vacuo. 53 g of 3-fluoro-4-amino-trifluoromethoxy-benzene distil over at a boiling point of 68 to 69° C. at 20 mbar.

Example IV-3

(a)

90 g of 4-trifluoromethoxy-fluorobenzene are introduced into a stirring apparatus, and 105 g of mixed acid (33% by weight nitric acid, 67% by weight sulphuric acid) are added dropwise at 10° to 15° C. The mixture is stirred for a further 2 hours at 20° C. and is then poured onto ice. The organic phase is separated off with the aid of dichloromethane, and the solution is dried and distilled. An amount of 112 g of a mixture consisting of 43% by weight of 3-nitro-4-fluoro-trifluoromethoxy-benzene and 54% by weight of 2-nitro-4-fluoro-trifluoromethoxy-benzene distils over in a boiling range of 90° to 94° C. at 15 mbar.

(b)

112 g of the nitro compounds obtained in a) in 450 ml of methanol together with 12 g of Raney nickel are introduced into a hydrogenation apparatus, and hydrogenation is carried out with 30 bar hydrogen at 25° to 45° C. After cooling and releasing the pressure, the mixture is filtered, and the filtrate is then subjected to precision distillation. 32 g of 2-amino-4-fluoro-trifluoromethoxybenzene distilled over in a boiling range of 58° to 60° C. at 14 mbar, and 28 g of 3-amino-4-fluoro-trifluoromethoxybenzene distilled over after an intermediate cut at 64 to 65° C. and 15 mbar.

EXAMPLE IV-4

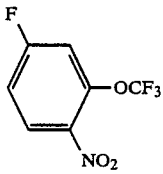
(a)

83 g of 3-trifluoromethoxy-fluorobenzene are nitrated with 100 g of nitrating acid at 15° C., in analogy with Example IV-3. The reaction mixture is worked up analogously, and consists of 78% by weight of 3-fluoro-4-amino-trifluoromethoxy-benzene and 20% by weight of 3-fluoro-6-nitro-trifluoromethoxy-benzene. The total yield was 99 g.

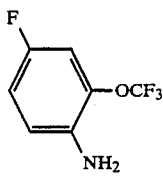
(b)

In 350 ml of methanol, the 99 g of nitro compounds prepared in a) are hydrogenated at 25° to 40° C. and with 30 to 50 bar hydrogen in a hydrogenation apparatus and in the presence of 10 g of Raney nickel. When the hydrogen uptake is complete, the mixture is cooled and the pressure is released, the solid components of the reaction mixture are filtered off, and the solvent is then removed by distillation. In the boiling range of 53° to 54° C. at 10 mbar, precision distillation of the residue yielded 5 g of 3-fluoro-6-amino-trifluoromethoxybenzene, and, in a boiling range of 56° to 57° C. at 10 mbar and after intermediate cut, it yielded 38 g of 3-fluoro-4-amino-trifluoromethoxy-benzene.

EXAMPLE IV-5

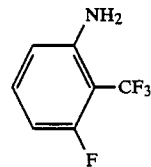

100 g of 2,6-difluorobenzotrifluoride in 300 ml of tetrahydrofuran are introduced into a stainless steel autoclave, and 30 ml of liquid ammonia are forced in. The mixture is heated stepwise to 125° C., and is stirred for a further 5 hours at this temperature. The mixture is cooled to 20° C., the pressure is released, and the solution is distilled under reduced pressure. 46 g of 2-amino-6-fluoro-benzotrifuoride distil over at a boiling point of 49° to 50° C. at 8 mbar.

EXAMPLE IV-6

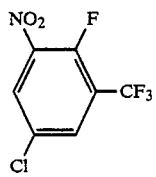
(a)

100 g of 2-fluoro-5-chloro-benzotrifluoride are introduced into a stirring apparatus, and 120 g of nitrating acid (33% by weight nitric acid and 67% by weight sulphuric acid) are added dropwise at 40° C. The mixture is stirred for a further hour at 40° to 45° C., then cooled and poured onto ice. The organic phase is extracted with dichloromethane, dried and distilled. At a boiling point of 92° to 94° C. at 18 mbar, 112 g of nitro compounds containing 91.3% by weight of 2-fluoro-5-chloro-3-nitrobenzotrifluoride distil over.

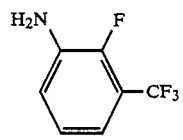
(b)

111 g of the nitro compounds obtained in a) are introduced in 500 ml of tetrahydrofuran into a hydrogenation apparatus and 50 g of triethylamine and 15 g of Raney nickel are added in succession. The apparatus is flushed with hydrogen, and the reaction mixture is hydrogenated at 25° to 120° C. at a hydrogen pressure of 30 to 80 bar. When hydrogen uptake is complete, the mixture is cooled and the pressure is released. The reaction mixture was filtered, the filter residue was washed with tetrahydrofuran, and the filtrates were combined, and most of the tetrahydrofuran was distilled off on a column, under atmospheric pressure. The bottom was stirred with 200 ml of water, the organic phase was then separated off, dried, and subjected to precision distillation under reduced pressure. At a boiling point of 70° to 72° C. at 16 mbar, 52 g of 2-fluoro-3-amino-benzotrifluoride distilled over.

EXAMPLE V-1

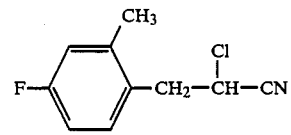

40 ml of 25 per cent hydrochloric acid and 28.8 ml (0.37 mole) of acrylonitrile are added to 15 g (0.12 mole) of 4-fluoro-2-methylaniline in 40 ml of acetone, 8.7 g (0.13 mole) of sodium nitrite in 17 ml of water are then added dropwise and with stirring in the course of one hour at 0° C. to 10° C., and the mixture is stirred for a further hour at 0° C. to 10° C., and several portions of copper(II) oxide powder are then added, with nitrogen gas vigorously evolving. When the evolution of gas is complete, the mixture is stirred for a further 15 hours at room temperature, dichloromethane is then added, the mixture is washed with water, dried over sodium sulphate and concentrated in vacuo, and the oily residue is purified by chromatography on silica gel (mobile phase: cyclohexane/ethyl acetate 1:1).

44.2 g (89.3% of theory) of 2-chloro-3-(4-fluoro-2-methylphenyl)-propionitrile are obtained as an oil. $^1$H-NMR* (CDCl$_3$/TMS) : δ=3.3 (2 H); 6.9 (2 H); 4.5 (1 H); 7.2 (1 H); 2.4 (3 H) ppm.

In a corresponding manner, Example V-2 is obtained:

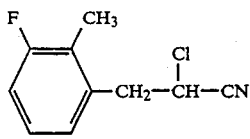

$^1$H-NMR* (CDCl$_3$/TMS) : δ=2.3 (3 H); 3.35 (2 H); 4.5 (1 H); 7.0 (2 H); 7.15 (1 H) ppm. *) The 1H-NMR spectra were recorded in deuterochloroform (CDCl$_3$) with tetramethylsilane (TMS) as the internal standard. Data refer to the chemical shift as δ-value in ppm.

Use Example

In the following use example, the compound listed below was employed as a comparison substance:

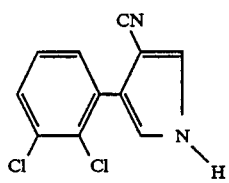

(A)

3-cyano-4-(2,3-dichlorophenyl)-pyrrole (cf. EP 174,910 and EP 236,272).

EXAMPLE A

Botrytis test (bean)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the size of the infected spots on the leaves is evaluated.

In this test, for example, the compound$of Preparation Examples 1-5 has a clearly superior activity as compared with the prior art.

EXAMPLE B

Leptosphaeria nodorum-test (wheat) / protective

Solvent: 100 parts by weight dimethylformamide
Emulsifier: 0,25 parts by weight alkylarylpolyglycolether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidium suspension of *Leptosphaeria nodorum*. The plants remain in an incubation cabin at 20° C. and 100% relative atmospheric humidity for 48 hours.

The plants are placed in a greenhouse at a temperature of about 15° C. and a relative atmospheric humidity of about 80%.

Evaluation is carried out 10 days after the inoculation.

In this test, a clearly superior activity compared with the prior art is shown, for example, by the compound according to the preparation example : 7

EXAMPLE C

*Fusarium nivale* test (rye) / seed treatment

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

2 batches of 100 grains of the rye are sown 1 cm deep in standard soil and are cultivated in a greenhouse at a temperature of about 10° C. and a relative atmospheric humidity of about 95% in seedboxes which are exposed to light for 15 hours daily.

About 3 weeks after sowing, the plants are evaluated for symptoms of snow mold,

In this test, a clearly superior activity compared with the prior art is shown, for example, by the compound according to the example 1.

What I claim is:

1. A 3-cyano-4-phenyl-pyrrole of the formula

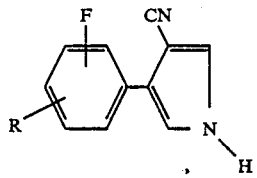

in which
  R stands for halogen, alkyl, alkoxy, alkylthio, halogenoalkyl, halogenoalkoxy or halogenoalkylthio.

2. A 3-cyano-4-phenyl-pyrrole according to claim 1, in which
  R stands for fluorine; chlorine; bromine; iodine; alkyl, alkoxy or alkylthio, each having 1 to 4 carbon atoms; or halogenoalkyl, halogenoalkoxy or halogenoalkylthio, each having 1 to 4 carbon atoms and 1 to 9 identical or different halogen atoms.

3. A 3-cyano-4-phenyl-pyrrole according to claim 1, in which
  R stands for fluorine, chlorine, bromine, methyl, ethyl, methoxy, ethoxy, methylthio, trifluoromethyl, trifluoromethoxy or trifluoromethylthio.

4. A 3-cyano-4-phenyl-pyrroles according to claim 1, in which

R stands for fluorine, chlorine, methyl, trifluoromethyl or trifluoromethoxy.

5. A method of combating fungi comprising applying to said fungi or an environment thereof a fungicidally effective amount of at least one 3-cyano-4-phenyl-pyrrole according to claim 1.

6. A fungicidal composition comprising a fungicidally effective amount of at least one 3-cyano-4-phenyl-pyrrole according to claim 1 and a suitable extender.

* * * * *

UNITED STATES PATENT AND TRADEMARK OFFICE
CERTIFICATE OF CORRECTION

PATENT NO.   : 4,960,789

DATED        : October 2, 1990

INVENTOR(S)  : Wollweber et al.

It is certified that error appears in the above-identified patent and that said Letters Patent is hereby corrected as shown below:

Title Page      [54] Invention: After "PYRROLES " insert -- AS FUNGICIDES --

Signed and Sealed this

Twenty-first Day of July, 1992

*Attest:*

DOUGLAS B. COMER

*Attesting Officer*      *Acting Commissioner of Patents and Trademarks*